(12) United States Patent
Huang et al.

(10) Patent No.: US 7,860,688 B2
(45) Date of Patent: Dec. 28, 2010

(54) SIGNAL BASELINE PROCESSING DEVICE AND PROCESSING METHOD THEREOF

(75) Inventors: Daxin Huang, Shenzhen (CN); Xing Shi, Shenzhen (CN); Tianfeng Zhao, Shenzhen (CN); Huan Qi, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 466 days.

(21) Appl. No.: 11/965,640

(22) Filed: Dec. 27, 2007

(65) Prior Publication Data

US 2009/0018799 A1    Jan. 15, 2009

(30) Foreign Application Priority Data

Jul. 13, 2007    (CN)    .................. 2007 1 0075884

(51) Int. Cl.
*H04B 15/06* (2006.01)
(52) U.S. Cl. .................. 702/190; 702/183; 702/193; 702/198
(58) Field of Classification Search .................. 702/50, 702/85, 89, 109, 128, 176, 178, 190; 348/750; 360/46; 378/53, 55
See application file for complete search history.

(56) References Cited

U.S. PATENT DOCUMENTS 5,675,517 A * 10/1997 Stokdijk ...................... 702/85
5,684,850 A * 11/1997 Warburton et al. ............. 378/53
5,873,054 A * 2/1999 Warburton et al. .......... 702/190

2007/0103806 A1    5/2007    Esumi et al.

FOREIGN PATENT DOCUMENTS

| CN | 1077830 A | 10/1993 |
|---|---|---|
| CN | 1157856 C | 8/2002 |
| JP | 200787538 | 4/2007 |
| JP | 2007087538 | 4/2007 |

OTHER PUBLICATIONS

Laing Chen & Dong Miao, Solution of Baseline Drift in Optical Fiber Transmission Network, 13(3) Electronics Optics & Control 85 (Jun. 2006) (Chinese).
Wu-Yun Xiao, Yi-Xiang Wei & Xian-Yun Ai, Digital Baseline Estimation Method for multi-channel Pulse Height Analyzing, 25(6) Nuclear Electronics & Detection Technology 601 (Nov. 2005) (Chinese).

* cited by examiner

*Primary Examiner*—Eliseo Ramos Feliciano
*Assistant Examiner*—Felix E Suarez
(74) *Attorney, Agent, or Firm*—Kory D. Christensen; Stoel Rives LLP

(57) ABSTRACT

A baseline processing device and method are provided for analyzing signals with uneven distributions of pulses and slow varying baselines. In one embodiment, the device includes an A/D sampling unit for sampling a digital counting signal to obtain sampled data, and a baseline extracting unit for sorting the N sampled data in the sampling sequence by magnitude and for outputting, among the N sample data, one sample data A with a value equal to the mid-value in the N sample data. A phase compensating unit with a width of M, to which a digital signal is input, outputs a sampled data B according to a FIFO sequence, wherein M=N/2. A first subtractor subtracts the sample data A from the sample data B and outputs the result as baseline removed data.

20 Claims, 10 Drawing Sheets

US 7,860,688 B2

SIGNAL BASELINE PROCESSING DEVICE AND PROCESSING METHOD THEREOF

RELATED APPLICATIONS

The present application claims priority to Chinese Patent Application No. 200710075884.7, filed Jul. 13, 2007, which is hereby incorporated by reference in its entirety.

TECHNICAL FIELD

The present disclosure relates to a device and method for processing signals, and particularly to a device and method for processing signal baselines.

SUMMARY

A baseline processing device and method are provided for analyzing signals with uneven distributions of pulses and slow varying baselines.

DETAILED DESCRIPTION

Figure 1:
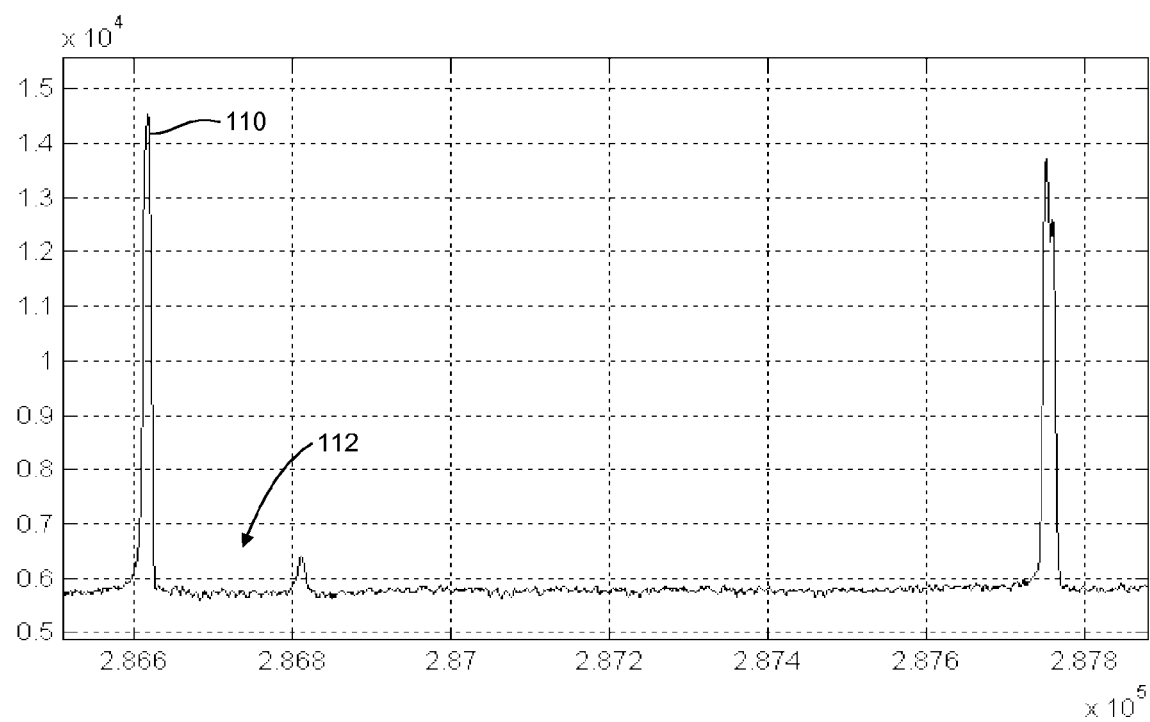
FIG. 1 is a schematic diagram showing a pulse waveform generated by a particle passing through a gemstone aperture.

During measurement of a signal corresponding to a physical condition or parameter, the signal's baseline may fluctuate due to external interferences. When the measurement includes the detection of pulse amplitudes within the signal, the slowly fluctuating baseline may affect the detection accuracy of the amplitudes of the pulses in the signal. For example, in a particle analyzing apparatus (such as a blood cell analyzer), a cell volume can be determined by a peak value of a pulse. While a particle (such as a blood cell) is flowing through a sensor (e.g., a gemstone aperture), an electric pulse 110, whose amplitude is proportional to the volume of the particle, is generated in a particle counting signal 112, as shown in FIG. 1. After amplification, filtering and analog-to-digital (A/D) conversion, the particle counting signal 112 is converted into a digital counting signal. After the digital counting signal is data compressed, stored and detected for the pulse peak value, the information on the volume of the blood cell is determined.

Figure 2:
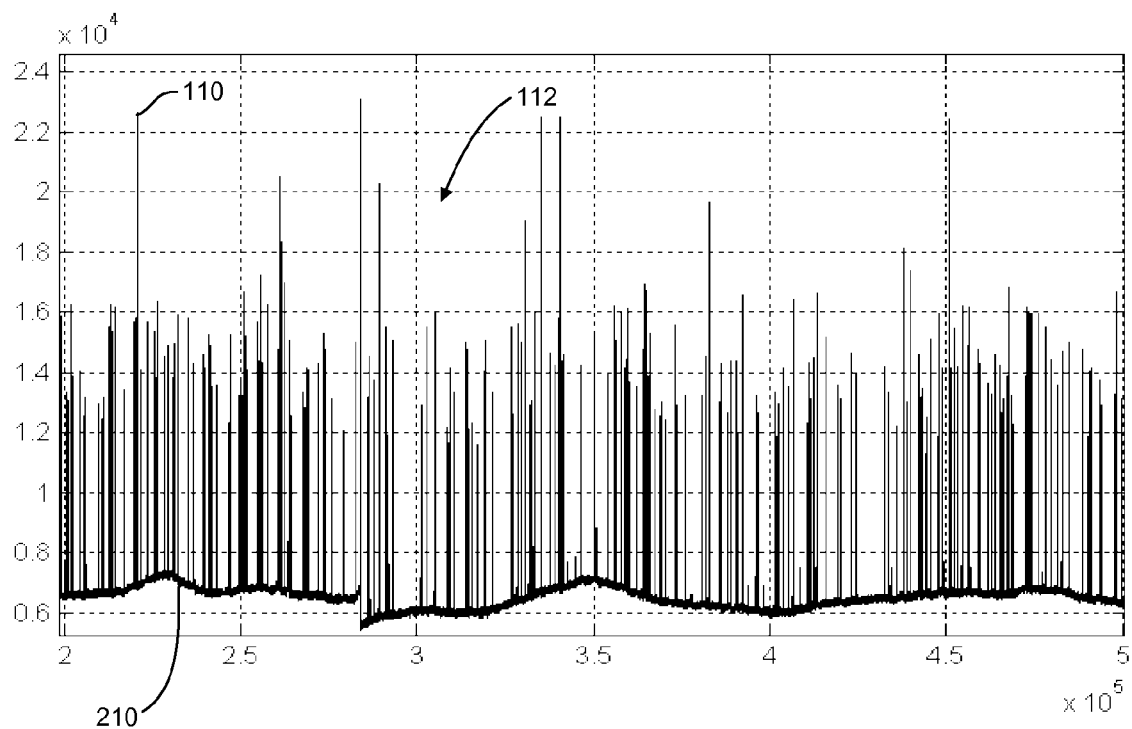
FIG. 2 is a schematic diagram showing a slow shift of a baseline.

Due to external interferences, however, there may be a baseline fluctuation in the particle counting signal 112. As shown in FIG. 2, such external interferences generally influence system performance in the form of a fluctuating baseline 210 that is superimposed on the counting signal 112. The fluctuating baseline 210 increases or decreases the pulse peak values and affects the accuracy of pulse peak value detection in the digital counting signal.

The fluctuating baseline 210 also affects the compression ratio of the digital counting signal. Because the particle pulse in the digital counting signal is narrow, a high sampling rate is generally used to acquire enough information on the particle pulse 110. To acquire adequate pulse samples, a long sampling time is used. Therefore, the size of the digital counting signal is generally large and may need to be compressed to reduce storage requirements.

Figure 3:
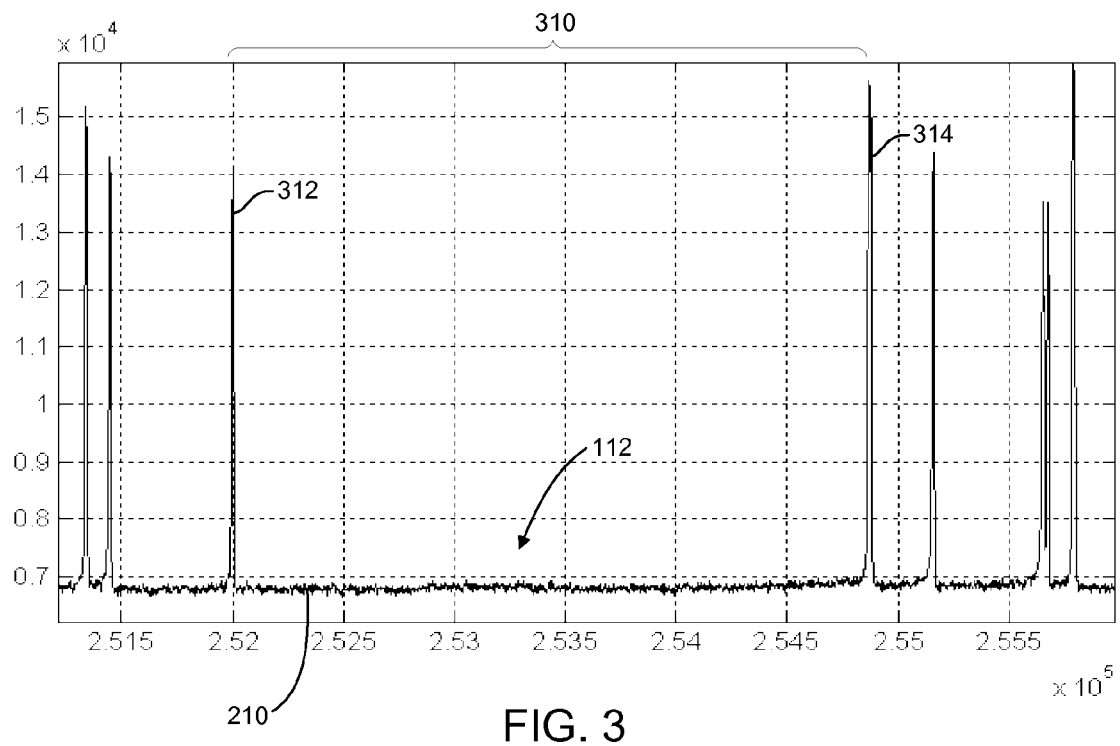
FIG. 3 is a schematic diagram of spacing between pulses.

As shown in FIG. 3, the spacing 310 between two consecutive particle pulses 312, 314 may be large. Such a spacing 310 between the particle pulses 312, 314 is generally useless for pulse peak value detection. Thus, the spacing 310 may be removed by compression so that information transmitted to a central processing unit (CPU) can be dealt with for storage and detection.

One compression method is to set a fixed output threshold, and output data if it is larger than the threshold so as to remove the spacing 310 between the cell pulses 312, 314. In the presence of the baseline fluctuation 210, the amplitude of a pulse in the digital counting signal is generally removed from the signal or distorted if the selected output threshold is too high, and the compression ratio will deteriorate if the threshold is too low.

Figure 4:
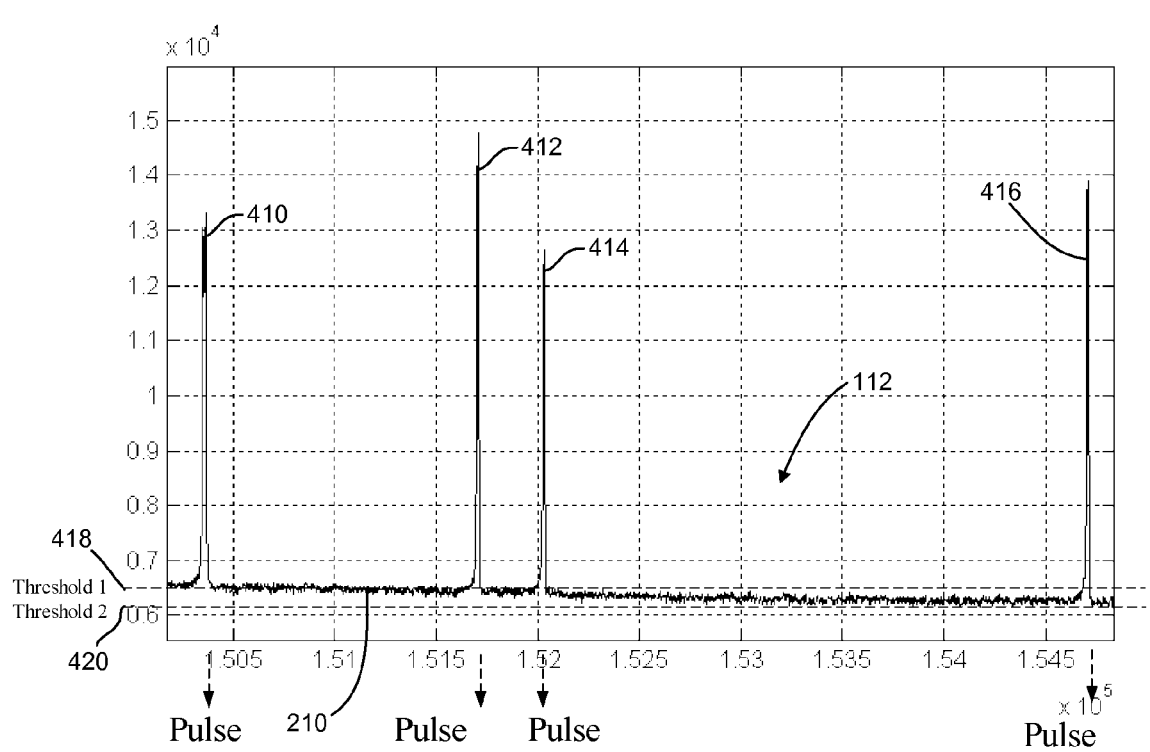
FIG. 4 is a schematic diagram illustrating a threshold setting for pulses.

FIG. 4 illustrates a particle counting signal 112 that has a first pulse 410, a second pulse 412, a third pulse 414, and a fourth pulse 416. FIG. 4 also illustrates a first threshold 418 and a second threshold 420. As shown in FIG. 4, the spacing between the first pulse 410 and the fourth pulse 416 cannot be removed if the second threshold 420 is selected because substantially the entire counting signal 112 is above the second threshold 420. Further, the amplitudes of the second pulse 412, third pulse 414 and fourth pulse 416 will be distorted if the first threshold 418 is selected. Because the baseline 210 may be below the first threshold 418 while it fluctuates, the parts of the pulses 412, 414, 416 below the first threshold 418 in the counting signal 112 will not be output, causing the pulse amplitudes to be distorted and any pulses with relatively low amplitudes (e.g., below the first threshold 418) to be lost.

In conventional systems, accurate recognition of the baseline 210 generally depends on accurate estimation of the duration period of a pulse. After the baseline 210 is recognized, pulse recognition is carried out by subtracting the baseline 210 from the digital counting signal. Accordingly, a contradiction arises in that the accurate recognition of the baseline 210 requires the accurate determination of the pulse duration, while the accurate recognition of the pulse requires in turn the accurate recognition of the baseline 210. Therefore, the conventional baseline recognition technology generally has poor universality in that the variation of the characteristics of the counting signal 112 exert an influence on the determination of the duration of the pulse, and thus on the recognition of the baseline, and hence on the accurate recognition of peak value of the pulse. The conventional baseline recognition technology is also generally complex and difficult to use because recognition of the baseline 210 and the pulse characteristic value (including the starting point, the peak value and the ending point of the pulse) interact with each other, which leads to more complicated processing and more difficulty in debugging.

The baseline processing device and method of the present disclosure solves the problems of conventional techniques by providing a device and a method for processing a signal baseline, in which the baseline in a particle counting signal is substantially removed and the adverse influence on the accuracy of pulse peak recognition and data compression ratio by the baseline is reduced or eliminated.

To achieve the above objective, the present disclosure provides a signal baseline processing device, comprising an analog-to-digital (A/D) sampling unit for sampling a digital counting signal to obtain sample data during a plurality of time periods. The signal baseline processing device also comprises a baseline extracting unit, to which the sample data are input, configured to sort N sample data in a sampling sequence by magnitude each time period, and output, among the N sample data, one sample data A with a value equal to or smaller than a mid-value in the N sample data, wherein a distribution width of the N sample data in the counting signal is substantially larger than a width of a single pulse in the counting signal, smaller than a baseline shift width, and larger than twice the sum of widths of all pulses in the distribution width.

In one embodiment, the signal baseline processing device also comprises a phase compensating unit with a width of M, to which the sample data are input, configured to output a sample data B according to a first-in-first-out (FIFO) sequence, wherein M=N/2, as well as a first subtractor, to which the sample data A and the sample data B are input, configured to subtract the sample data A from the sample data B, and output the result as baseline removed data.

The present disclosure also provides a method for processing a signal baseline, comprising sampling a counting signal to obtain sample data during a plurality of time periods. The method also comprises sorting N sample data each time in a sampling sequence by magnitude, and outputting, among the N sample data, an arbitrary sample data A with a value equal to or smaller than a mid-value of the N sample data. In one embodiment, the distribution width of the N sample data in the counting signal is substantially larger than a width of a single pulse in the counting signal, smaller than a baseline shift width, and larger than twice the sum of widths of all pulses in the distribution width.

In one embodiment, the method also includes selecting a ½Nth sample data B of the N sample data in the sampling sequence, subtracting the sample data A from the sample data B; and outputting the result of the subtraction of the sample data A from the sample data B as baseline removed data.

Advantageously, the disclosed method and device output a baseline value from sampled data with a mid-value filtering algorithm, subtracts the baseline value from a counting signal, removes the influence on pulse amplitudes by the baseline, and thus separates the baseline processing and the pulse recognition. Therefore, the recognitions of the baseline and the pulse characteristic values will not interfere with each other, and debugging can be easily performed. The disclosed method and device can adapt to variations of characteristics of various signals by setting the number N of sampled data to be sorted. The disclosed method and device are also highly efficient. To ensure real time operation, the ordinary mid-value filtering algorithm can only handle N sampled data to be sorted with N smaller than 10; and with the same resources, the disclosed method and device create a storage space, count the sampled data with the same value as a whole in sorting, and thus perform mid-value filtering for thousands of sampling points quickly. Therefore, the disclosed method and device are suitable for a high-speed signal sampling system.

First Example Baseline Processing Device

Figure 5:
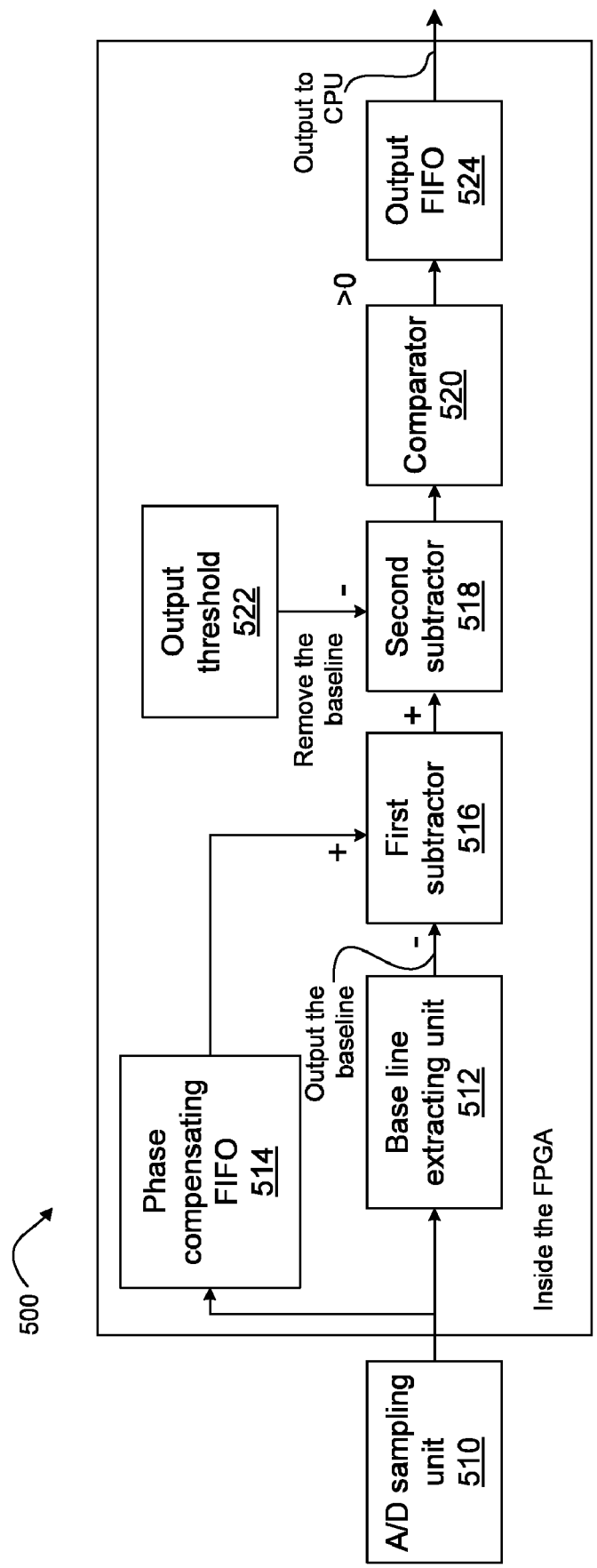
FIG. 5 is a structural schematic diagram showing an example baseline processing device according to one embodiment.

Referring to FIG. 5, a baseline processing device 500 includes an A/D sampling unit 510, a baseline extracting unit 512, a phase compensating unit 514, a first subtractor 514, a second subtractor 518, and a comparator 520. The A/D sampling unit 510 is used to sample a counting signal for obtaining sample data. The baseline extracting unit 512, to which the sample data are input, sorts N sample data in a sampling sequence by magnitude and outputs an arbitrary sample data A of the N sample data, which is equal to or less than the mid-value. The distribution width of the N sample data in the digital counting signal is substantially larger than a single pulse width in the digital counting signal, smaller than a baseline shift width, and larger than twice the sum of the widths of all the pulses in the distribution width.

The phase compensating unit 514, to which the sample data are input, has a width of M for buffering M sampled data with M=½N. The phase compensating unit 514 outputs a sample data B in a first-in-first-out (FIFO) sequence. The first subtractor 516, to which the sample data A and the sample data B are input, subtracts the sample data A from the sample data B, and outputs the result as a baseline removed data. The second subtractor 518, to which the baseline removed data output by the first subtractor 516 and a fixed threshold value 522 are input respectively, subtracts the threshold value 522 from the baseline removed data, and outputs the result as a threshold removed data to the comparator 520. The comparator 520 is used to compare the threshold removed data with zero (0), and outputs the threshold removed data which is larger than zero (0).

Figure 6:
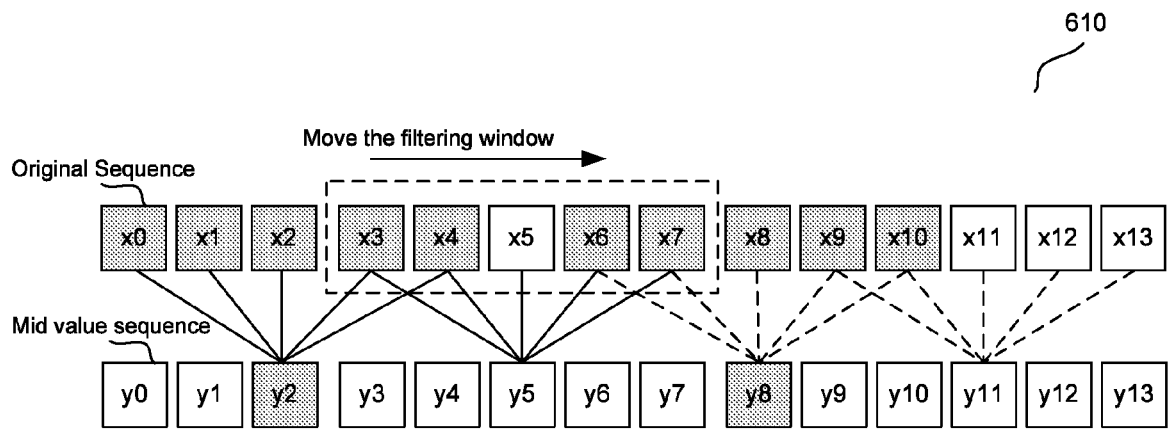
FIG. 6 is a schematic diagram of a mid-value filtering algorithm according to one embodiment.

The baseline extracting unit 512 processes the sample data to be sorted with a mid-value filtering algorithm, which begins with the head of the data to be sorted to acquire a number series with a fixed length sequentially (see the dotted box "window" 610 in FIG. 6), sorts the number series by magnitude, and outputs the data with a magnitude of the mid-value. The window 610 of the mid-value filtering algorithm with a width of fixed length moves from the data head to the data end to complete the processing.

Data in the window 610 are sorted into a number series by magnitude, and a number with a magnitude of the mid-value in the number series is output. The data processing is accomplished by moving the window 610 from the data head to the data end, and the portion of the baseline that is substantially wider than the window 610 is removed effectively without distorting the pulse with a width that is substantially smaller than that of the window 610.

Figure 7:
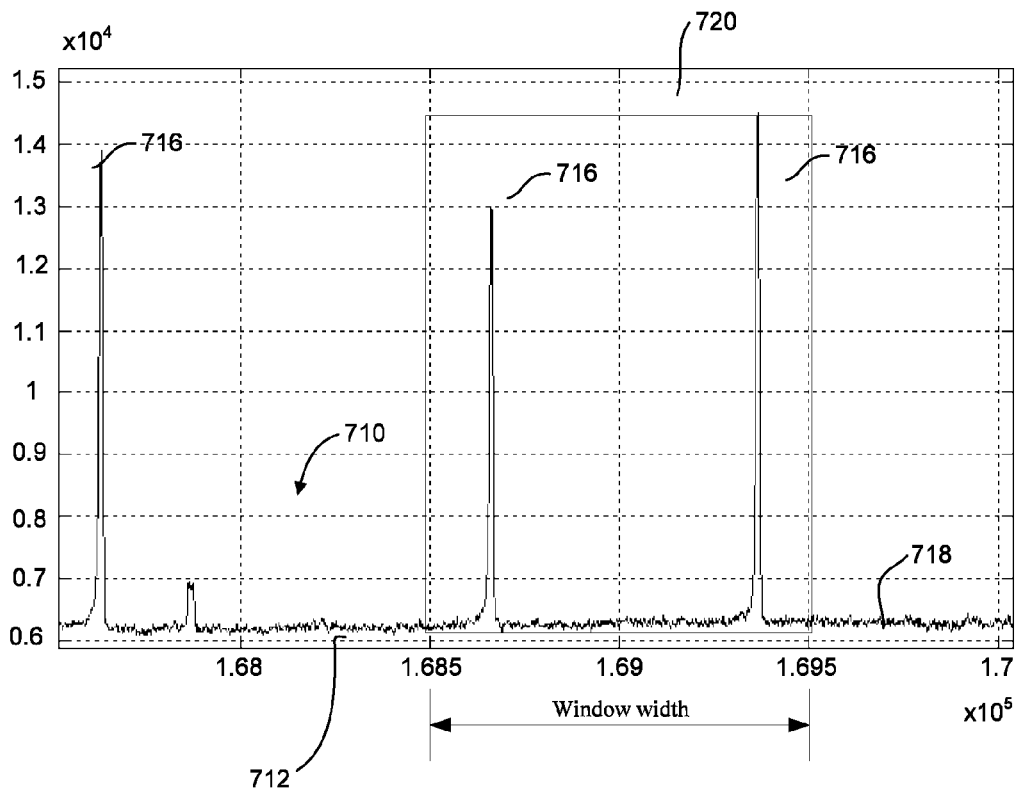
FIGS. 7, 8 and 9 are schematic diagrams illustrating the setting of a window width according to one embodiment.

As shown in FIG. 7, a digital count signal 710 has, as its components with their widths listed in a descending order: a baseline 712, bubble pulses, particle pulses 716 (three shown) and high-frequency noise 718. In one embodiment, the particle pulses 716 and bubble pulses remain in the digital count signal 710 while the baseline 712 is removed therefrom. Therefore, the baseline extracting unit 512 sets the distribution width (i.e., window width 720) of the N sample data to be sorted in the counting signal 710 such that the window width 720 is substantially larger than the widths of the particle pulses 716, the window width 720 is substantially smaller than that of the fluctuation of the baseline 712, and (at respective points in the digital counting signal 710) the sum of widths of all the particle pulses 716 in the window width 720 is not more than ½ the widow width 720.

The baseline extracting unit 512 sets the window width 720 such that it is substantially larger than the widths of the particle pulses 716, as shown in FIG. 7, so that the persistence points of the pulses (i.e., sampling points on the pulses), if included in the window 720, are all arranged on the larger end of the number series in the window 720.

Figure 8:
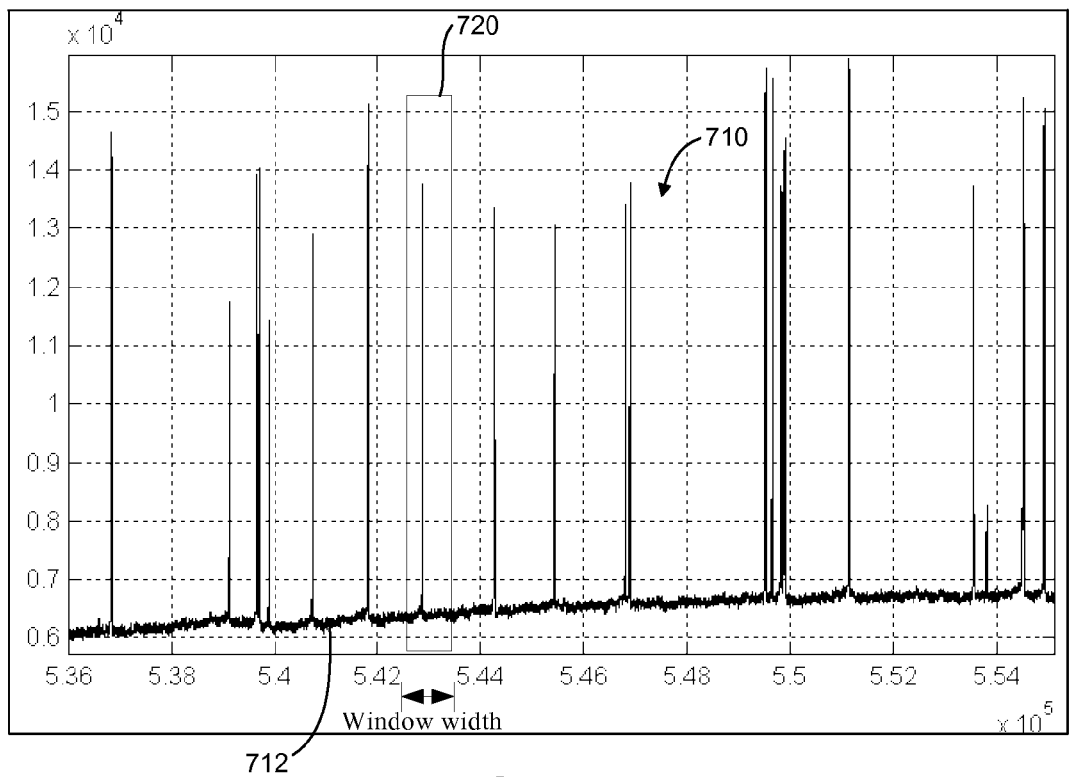

As shown in FIG. 8, the baseline extracting unit 512 sets the window width 720 substantially smaller than that of the baseline fluctuation so that the movement of the window 720 to one position in the digital counting signal 710 is equivalent to sampling the baseline 712 of the digital counting signal 710 with an output result close to the baseline value at this point in the digital counting signal 710.

Figure 9:
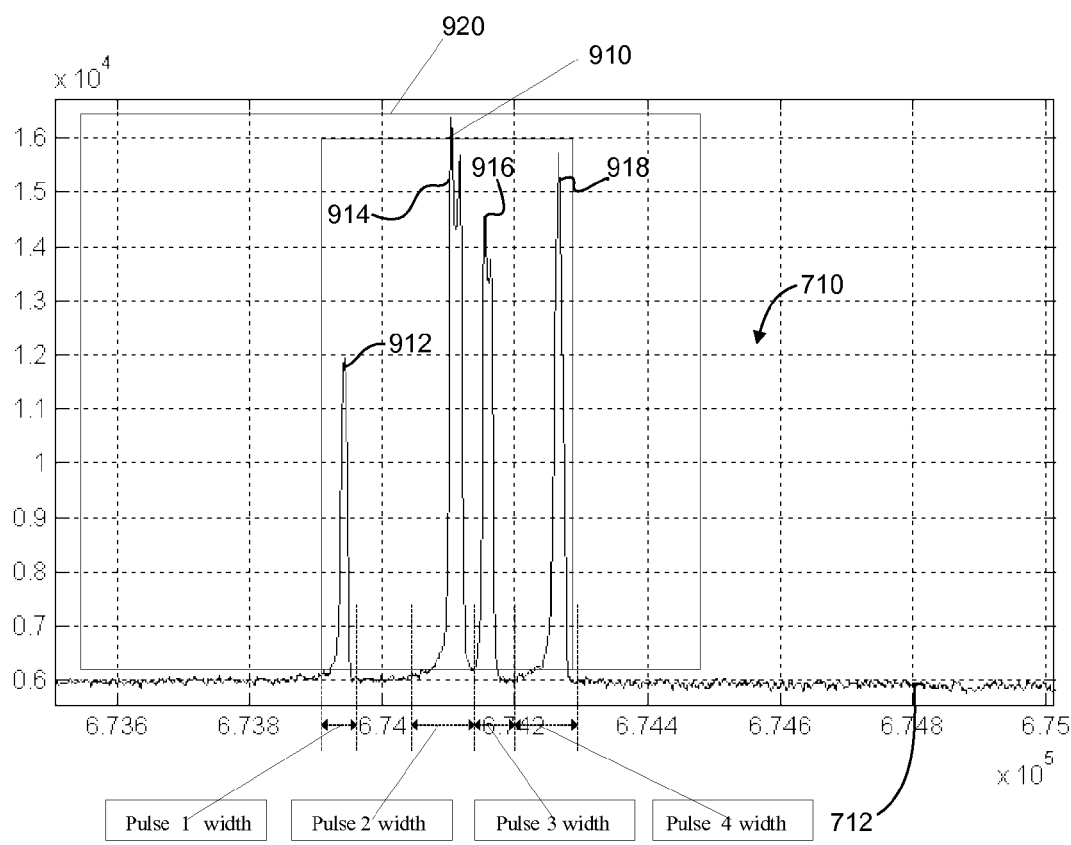

At respective points in the digital counting signal 710, the baseline extracting unit 512 sets the window width 720 such that the sum of the widths of all the particle pulses 716 in the window width 720 is not more than ½ of the window width 720. Otherwise, when the digital counting signal 710 is processed with the mid-value filtering algorithm, the values at the pulse persistence points may be output, causing the baseline 712 to have a pseudo rising and the amplitudes of the pulses 716 to be distorted. As shown in FIG. 9, when a window 910 is selected, the sum of the widths of the four pulses 912, 914, 916, 918 therein is more than ½ of the width of the window 910. In this case, the output result is not the real baseline 712 but the values at the pulse persistence points, and thus the recognized baseline is higher than what it really is. Furthermore, when another window 920 is selected, the sum of the widths of the four pulses 912, 914, 916, 918 in the other window 920 is not more than ½ of the width thereof, and therefore the baseline 712 can be recognized accurately.

Returning to FIG. 7, the window width 720 according to one embodiment is derived from the width of a particle pulse 716 and a time distribution of particles passing through a gemstone aperture. The width and the distribution are obtained through the flow speed of a particle passing through the gemstone aperture.

As useful information in the digital counting signal 710, the bubble pulses remain without any particular requirements about its completeness. Therefore, the window width 720 in one embodiment is more than twice that of the bubble pulses, and the points on the bubbles, if included, are arranged on the larger end of the number series in the window, not exceeding the midpoint of the number series to ensure that the values at the points on the bubbles will not be output in the mid-value filtering, and the bubble information will remain after the baseline 712 is removed.

When a suitable window width 720 is selected, the pulse persistence points in the N sample data are all arranged on the larger end of the number series in the window, and thus the output of the mid-value filtering is not affected by the values at the pulse persistence points. Therefore, as shown in FIG. 10, the particle pulse 716 in the digital counting signal 710 is output to the particle detection system (e.g., to a CPU through an output module 524, as shown in FIG. 5) without any distortion, the bubble pulse information remains and the baseline is removed.

Figure 11:
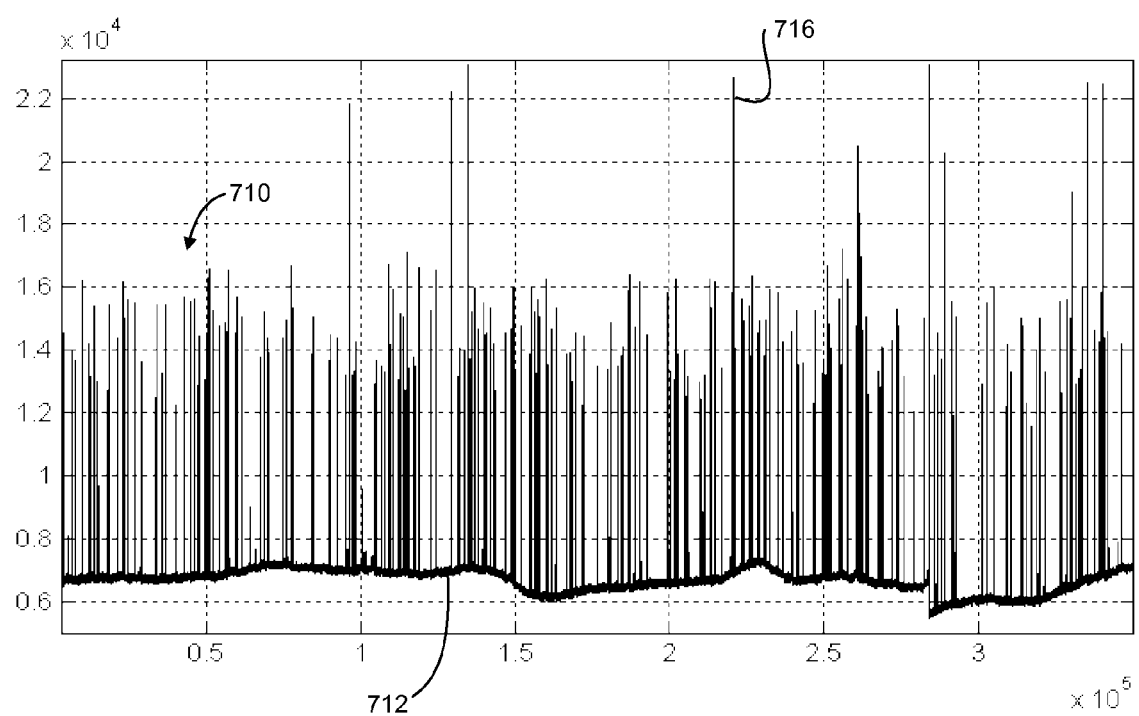
FIG. 11 is a schematic diagram of a counting signal including a baseline according to one embodiment.
Figure 12:
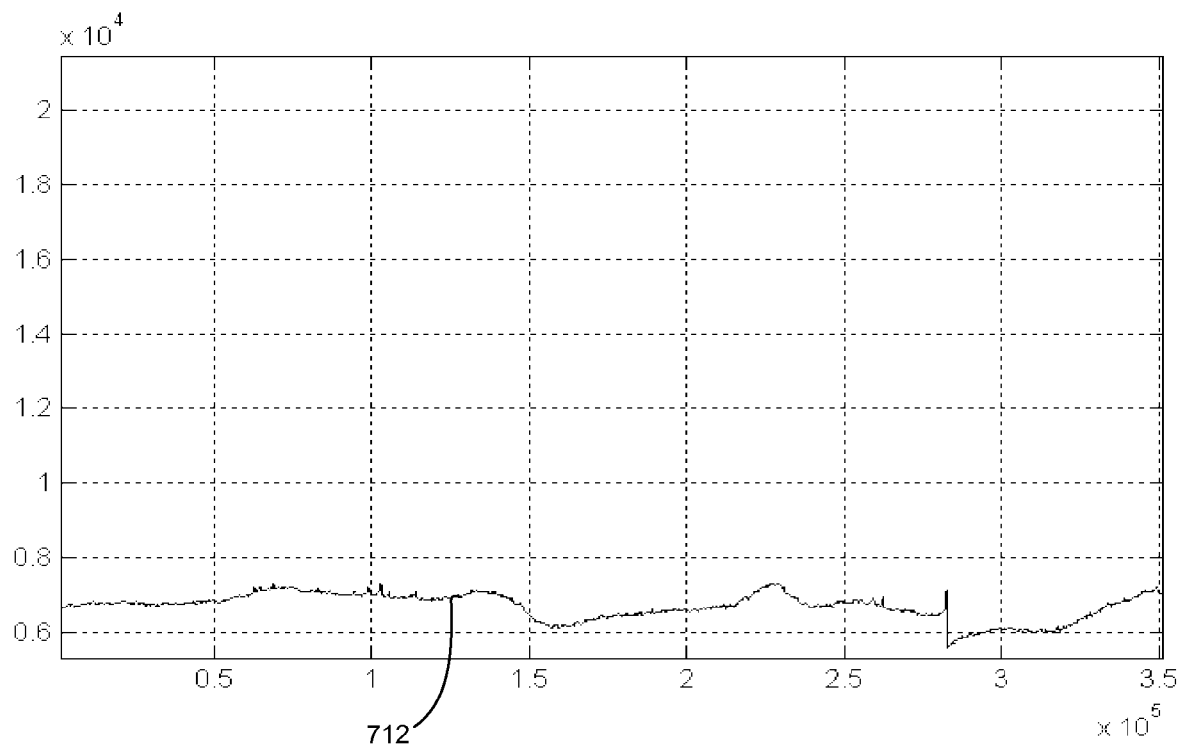
FIG. 12 is a schematic diagram showing the baseline illustrated in FIG. 11 extracted from a counting signal according to one embodiment.
Figure 13:
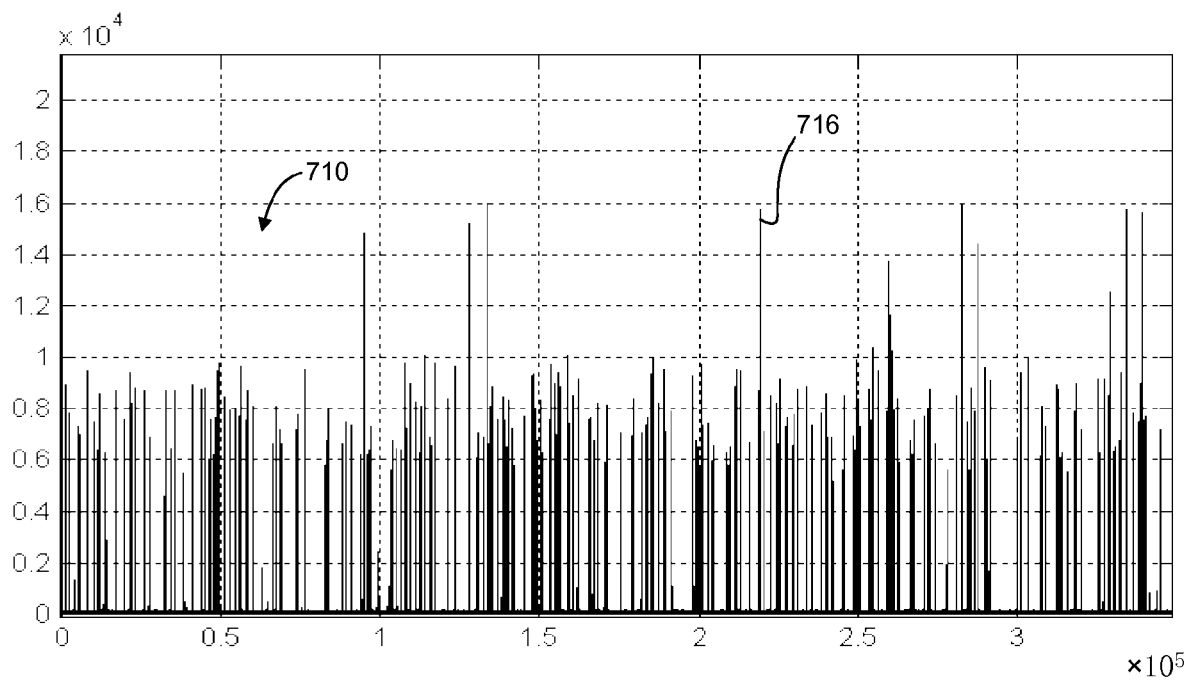
FIG. 13 is a schematic diagram showing the counting signal illustrated in FIG. 11 with its baseline removed according to one embodiment.

FIGS. 11, 12 and 13 illustrate the influence on the pulses 716 when the baseline is removed, wherein FIG. 11 shows the counting signal 710 including the baseline 712, with pulse amplitudes increased by the baseline 712, FIG. 12 shows the extracted baseline 712, and FIG. 13 shows the counting signal 710 with the baseline 712 removed.

The A/D sampling unit 510 shown in FIG. 5 samples an analog counting signal and inputs the sample data into the baseline extracting unit 512 and the phase compensating unit 514 simultaneously. The baseline extracting unit 512 sorts the input data, and once the sample data at N points have been received, it outputs a value with the mid-magnitude in the number series of the N points, that is, sample data A. The phase compensating unit 514 generally adopts a FIFO, which, as a phase compensating FIFO with a width of M, M=N/2, outputs the data of the first N/2 points when the data of the N points are input. Then, the number (i.e., the sampled data B), which the phase compensating unit 514 outputs at this time is the N/2th sampled data from which the sampled data A is subtracted to obtain the baseline removed data of the N/2th point.

Figure 10:
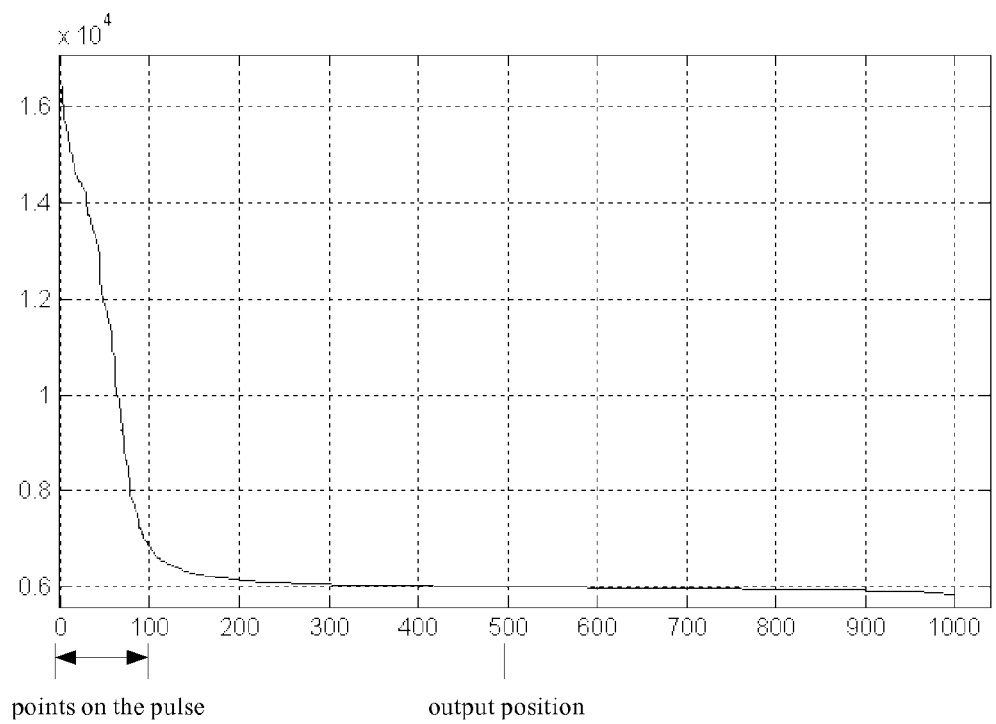
FIG. 10 is a schematic diagram showing the distribution of sorted sample data according to one embodiment.

In this embodiment, it should be understood by those skilled in the art that the sample data A output by the baseline extracting unit 512 can also be an arbitrary sample data smaller than the mid-value, as shown in FIG. 10. That is, the sample data behind the mid-value with respect to a descending order can be output as the baseline value. The baseline removed data at the point of the position of the sampled data B can be obtained by subtracting sampled A from sampled data B.

The second subtractor 518 subtracts the output fixed threshold 522 from the result obtained by subtracting the number output by the baseline extracting unit 512 from the number output by the phase compensating FIFO 514 to obtain the threshold removed data, which is compared with zero (0) by the comparator 520 and is output through an output FIFO 524 if it is larger than zero (0).

Then, the A/D chip 510 inputs the data of the next point, and the baseline extracting unit 512 deletes the first input sampled data. To output the baseline of the next point, the above-described process is repeated.

Second Example Baseline Processing Device

Figure 14:
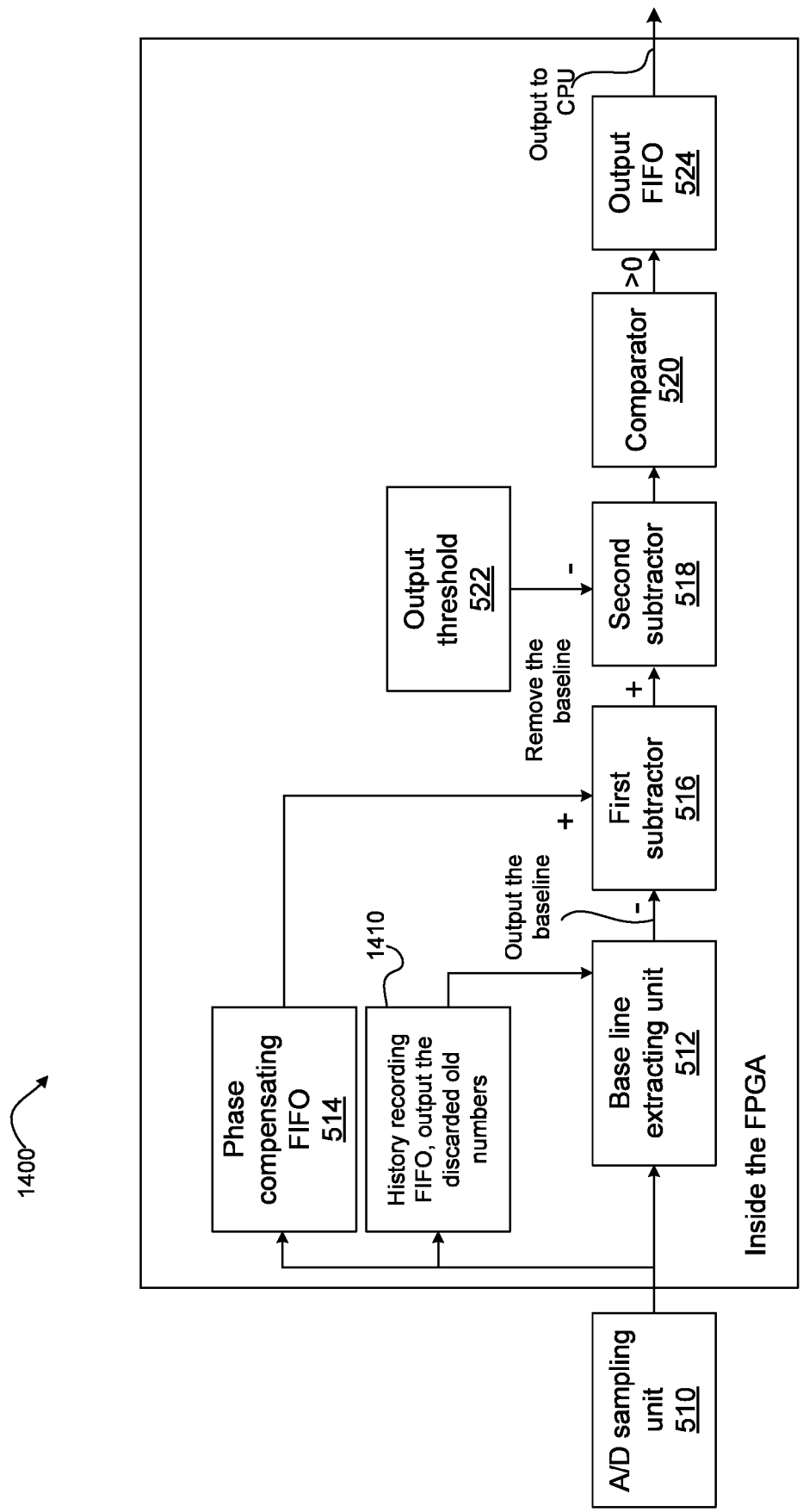
FIG. 14 is a structural schematic diagram showing another example baseline processing device according to one embodiment.

Referring to FIG. 14, an example baseline processing device 1400 includes an A/D sampling unit 510, a baseline extracting unit 512, a phase compensating unit 514, a history recording FIFO 1410, a first subtractor 516, a second subtractor 518, a comparator 520 and an output FIFO 524. The history recording FIFO 1410 has a width of N and is used to store data to be discarded. After sample data of N points are input and the baseline of the N/2th point is calculated with mid-value filtering by the baseline extracting unit 512, the data of the (N+1)th point is output by the A/D sampling unit 510 to the baseline extracting unit 512, the phase compensating unit 514 and the history recording FIFO 1410. In the history recording FIFO 1410, the first sampled data C in the digital counting signal 710 is output to the baseline extracting unit 512. Upon receiving the first sample data C output by the history recording FIFO 1410, the baseline extracting unit 512 deletes sample data C so that the sample data is not included in the next sorting. Thereafter, the baseline extracting unit 512 also sorts the 2nd to the (N+1)th points in the digital counting signal 710, and outputs the baseline of the (N/2+1) point. The baseline removed data and the threshold removed data are obtained according to the same method as that in the first example embodiment.

In this embodiment, the baseline extracting unit 512 may be controlled to delete the first sampled data in the N sampled data.

Third Example Baseline Processing Device

Figure 15:
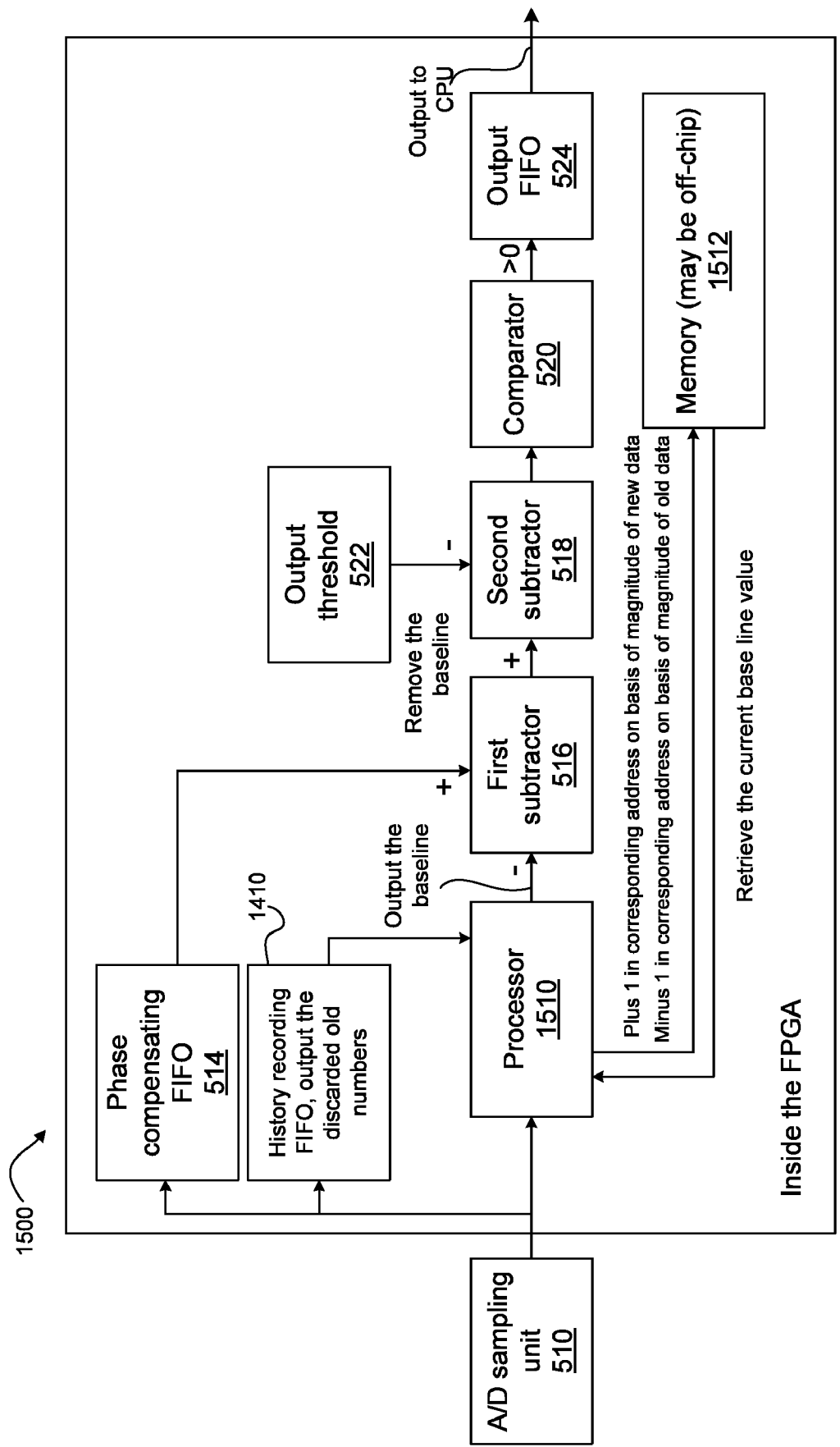
FIG. 15 is a structural schematic diagram showing yet another example baseline processing device according to one embodiment.

Referring to FIG. 15, an example baseline processing device 1500, which is similar to the first example embodiment 500 shown in FIG. 5 and the second example embodiment shown in FIG. 14, includes a processor 1510 and a memory 1512. The processor 1510 is used to receive and store N sample data to be sorted in storage space with the data values thereof as storage unit addresses in the memory and the number of the data of the same value as a storage value in the storage unit with corresponding address. Then, the processor 1510 accumulates the storage values in the storage space from the lowest to the highest addresses to determine the current accumulating address N1 at which the accumulated value is equal to (½N−P), wherein P is an integer selected from zero (0) (inclusive) to ½N on the basis of signal characteristics. In one embodiment, P is not allowed to be changed throughout the entire processing flow. The sample data A to be output is equal to the current accumulating address N1. When P=0, the sample data A to be output can be seen as the mid-value of the N sample data sorted in terms of magnitudes. When P>0, the sample data A to be output can be seen as the (½N−P)th sample data of the N sampled data sorted in ascending order.

Figure 16:
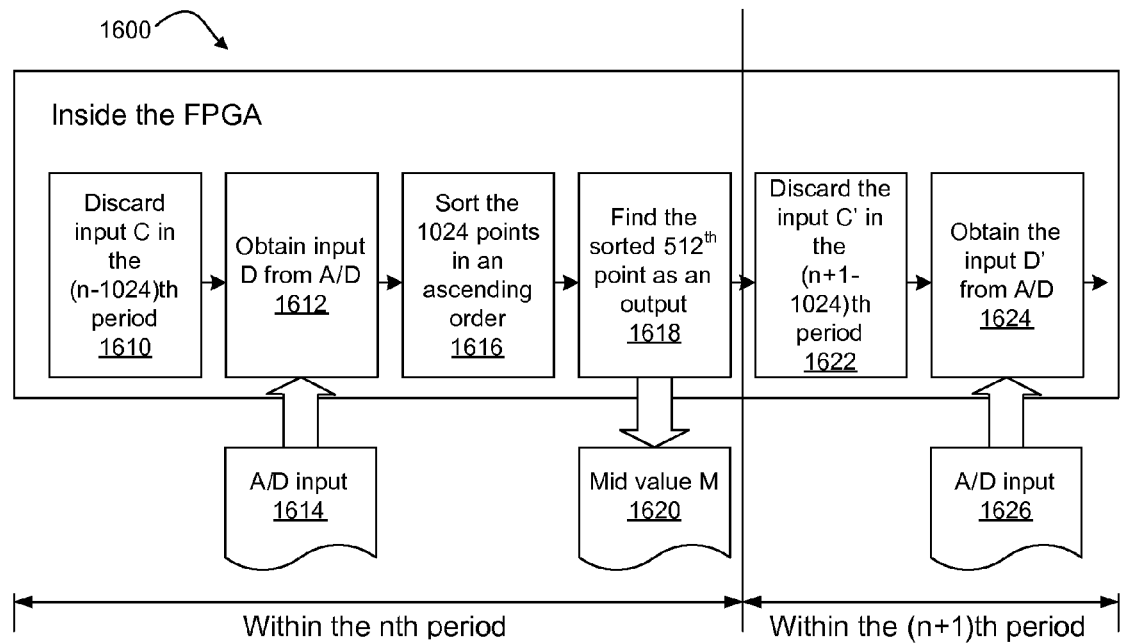
FIG. 16 is a flowchart of mid-value filtering by the example system shown in FIG. 15 according to one embodiment.

Because the window width 720 is designed to be relatively large (for example, the N sample data to be sorted can belong to as many as 4096 points), a rapid mid-value filtering algorithm is used in certain embodiments. A flowchart of such a mid-value filtering algorithm 1600 is shown in FIG. 16 (taking the N=1024 points as an example). The mid-value filtering algorithm 1600 is configured to sort the data with the same value as a whole. The mid-value filtering algorithm 1600 creates storage space into which the number series to be sorted is stored with data values thereof as addresses in the storage unit and the numbers of the data with the same values as storage values in the storage unit with corresponding addresses.

With reference to FIG. 16, the case that N is 1024 is described as an example. In short, the mid-value filtering algorithm 1600 includes within an nth period, discarding 1610 the input C in the (n−1024)th period, obtaining 1612 input D from an A/D input 1614 (e.g., the A/D sampling unit 510), sorting 1616 the 1024 points in an ascending order, and finding 1618 the sorted $512^{th}$ point as an output provided as mid-value M. Within an (n+1)th period, the mid-value filtering algorithm 1600 includes discarding 1622 the input C' in the (n+1−1024)th period, and obtaining 1626 the input D' from an A/D input 1626 (e.g., the A/D sampling unit 510).

Figure 17:
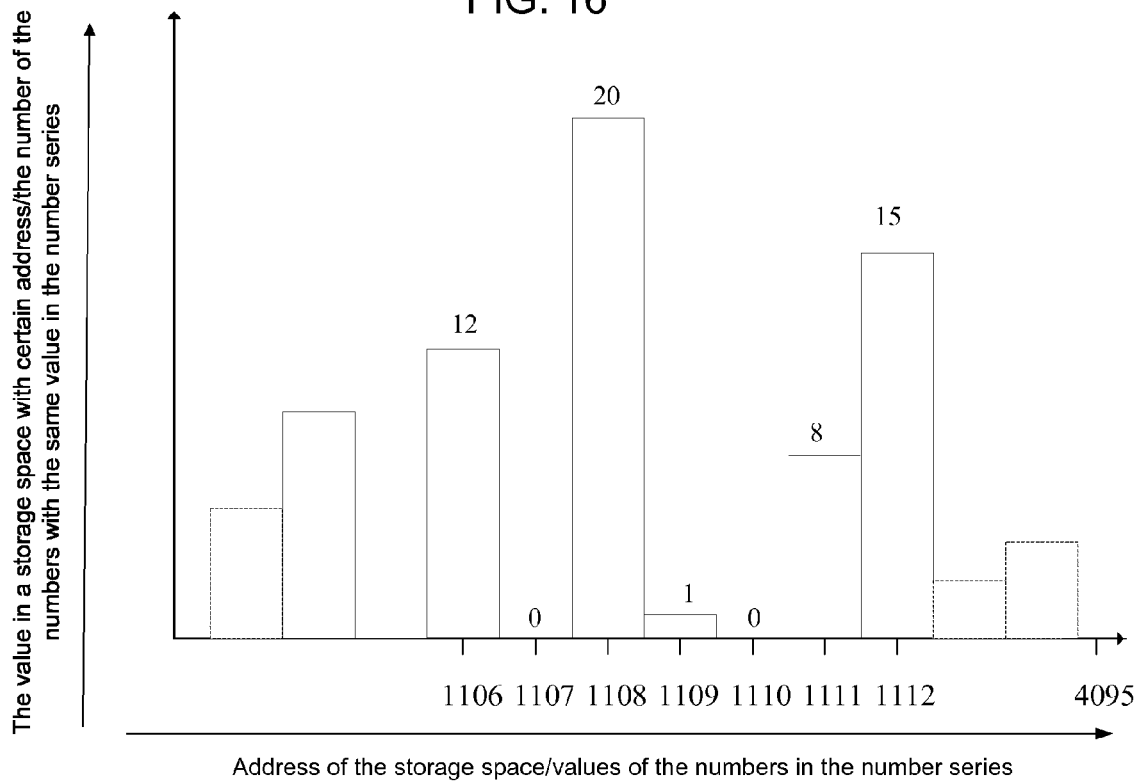
FIG. 17 is a schematic diagram showing a storage space address/value distribution in the system shown in FIG. 15 according to one embodiment.

The storage space may be considered as a data distribution histogram, with its horizontal axis representing data values (depending on the sampling precision, for example, if the precision is 12 bits, the horizontal axis is 0-4096), and its longitudinal axis representing the numbers of data (for example, if N is 1024, the data sum of the longitudinal axis is 1024). In FIG. 17, the value at 1106 on the horizontal axis is 12, that is, there are 12 numbers with the value of 1106 in the number series to be sorted. As another example, the value at 1108 on the horizontal axis is 20, that is, there are 20 numbers with the value of 1108 in the number series to be sorted.

To calculate the value E of the 512th number of the number series in ascending order, an integration is performed in the histogram shown in FIG. 17 to accumulate data in a direction from the lowest address zero (0) to higher addresses until the accumulated value (if there is further data in the current accumulating address N1) is equal to or larger than 512. Then, the mid-value E is equal to the address N1.

In one embodiment, the sampling is carried out continuously. In each period, new data is added to the number series and the oldest data is discarded at the same time. When the first sample data C is deleted, the storage value of the storage unit is the address C minus 1; and when a new sample data D is inserted, the storage value of the storage unit is the address D plus 1. Therefore, the sorting can be completed without any comparator operation only by performing reading/writing operations twice to the storage space in each period.

In certain embodiments, the baseline extracting unit 512, phase compensating unit 514, history recording register 1410, first subtractor 516, second subtractor 518 and comparator 520 may be embedded in a field programmable array (FPGA) chip, and the storage space of the baseline extracting unit 512 may be integrated inside or outside the FPGA. In a period of A/D sampling, a baseline calculation is performed for a sample point. Therefore, certain embodiments provide a real-time baseline processing method that does not increase measuring time.

The present disclosure can be applied to apparatuses for particle volume detection by measuring pulse signals with a sensor, which include, but are not limited to, medical appliances, laboratory analytical instruments, and the like, such as a blood cell analyzer, a urine analyzer, a bone marrow analyzer or a fluid-type cell analyzer. In addition, the present disclosure can also be applied to remove noises of pulse characteristics and output a slow varying signal.

A person of ordinary skill in the art will recognize that the described features, operations, or characteristics disclosed herein may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

It will be understood by those having skill in the art that many changes may be made to the details of the above-described embodiments without departing from the underlying principles of the invention. The scope of the present invention should, therefore, be determined only by the following claims.

What is claimed is:

1. A signal baseline processing device, comprising:
an analog-to-digital (ND) sampling unit for sampling a digital counting signal to obtain sample data during a plurality of time periods;
a baseline extracting unit, to which the sample data are input, configured to:
sort N sample data in a sampling sequence by magnitude each time period, and
output, among the N sample data, one sample data A with a value equal to or smaller than a mid-value in the N sample data,
wherein a distribution width of the N sample data in the counting signal is substantially larger than a width of a single pulse in the counting signal, smaller than a baseline shift width, and larger than twice the sum of widths of all pulses in the distribution width;
a phase compensating unit with a width of M, to which the sample data are input, configured to output a sample data B according to a first-in-first-out (FIFO) sequence, wherein M=N/2; and
a first subtractor, to which the sample data A and the sample data B are input, configured to subtract the sample data A from the sample data B, and output the result as baseline removed data.

2. The signal baseline processing device according to claim 1, further comprising:
a history recording FIFO memory, to which the sample data are input, configured to output an Xth sample data C to the baseline extracting unit after an (N+X)th sample data is input from the ND sampling unit, and wherein the baseline extracting unit is further configured to delete a current sample data C after receiving the Xth sample data C output by the history recording FIFO memory.

3. The signal baseline processing device according to claim 2, wherein the baseline extracting unit comprises a processor and a memory, wherein the processor is configured to receive a sample data each time period, and to add one (1) to a storage value in a storage unit of the memory with the value of the sample data as an address thereof.

4. The signal baseline processing device according to claim 3, wherein, when N data are input, the processor is further configured to accumulate the storage values of the data in the storage space from the lowest address of the storage unit to higher addresses, and to determine a current accumulating address N1 at which the accumulated value is equal to or larger than ½N.

5. The signal baseline processing device according to claim 4, wherein the output sample data A is selected from the storage unit whose address is equal to or smaller than the current accumulating address N1.

6. The signal baseline processing device according to claim 5, wherein the processor is further configured to subtract one (1) from the storage value in the storage unit with the same address as the value of the sample data C when it receives the sample data C output by the history recording FIFO memory, and to add one (1) to the storage value in the storage unit with the same address as the value of a newly input sample data D when the sample data D is input.

7. The signal baseline processing device according to claim 1, wherein the sample data A is the mid-value of the N sample data sorted by magnitude.

8. The signal baseline processing device according to claim 1, further comprising:
a second subtractor; and
a comparator,
wherein the baseline removed data output by the first subtractor and a threshold are respectively input to the second subtractor, the second subtractor configured to:
subtract the threshold from the baseline removed data and
input the result to the comparator as threshold removed data; and
wherein the comparator is configured to:
compare the threshold removed data with zero (0), and output the threshold removed data if it is larger than zero (0).

9. The signal baseline processing device according to claim 8, further comprising an output FIFO memory connected to an output terminal of the comparator.

10. A method for processing a signal baseline value in a signal baseline processing device, comprising:
sampling, using an analog-to-digital (A/D) sampling unit of the signal baseline processing device, a counting signal to obtain sample data during a plurality of time periods;
sorting N sample data each time in a sampling sequence by magnitude;
outputting, among the N sample data, an arbitrary sample data A with a value equal to or smaller than a mid-value of the N sample data,
wherein a distribution width of the N sample data in the counting signal is substantially larger than a width of a single pulse in the counting signal, smaller than a baseline shift width, and larger than twice the sum of widths of all pulses in the distribution width; and
selecting a ½Nth sample data B of the N sample data in the sampling sequence,
subtracting the sample data A from the sample data B; and
outputting the result of the subtraction of the sample data A from the sample data B as baseline removed data.

11. The method for processing a signal baseline according to claim 10, wherein sorting the N sample data comprises:
storing the sample data to be sorted in storage space with the values of the N sample data to be sorted as addresses of a storage unit and the numbers of the data of the same values as storage values in the storage unit with corresponding addresses;
accumulating the storage values of the data in the storage space from a lowest address to higher addresses to determine a current accumulating address N1 at which the accumulated value is equal to ½N−P, wherein P is an integer equal to or larger than zero (0) and smaller than ½N; and
means for outputting the current accumulating address N1 as the sample data A.

12. The method for processing a signal baseline according to claim 11, further including, after inputting a new sample data:
subtracting one (1) from the storage value in the storage unit with the same address as the value of a previous sample data of the N sample data, and adding one (1) to the storage value in the storage unit with the same address as the value of the newly input sample data.

13. The method for processing a signal baseline according to claim 10, wherein the sample data A is the mid-value of the N sample data sorted by magnitude.

14. A signal baseline processing system comprising:
means for sampling a digital counting signal to obtain sample data;
means for sorting N sample data in a sampling sequence corresponding to the sample data, and for outputting, among the N sample data, one sample data A with a value equal to or smaller than a mid-value in the N sample data,
wherein a distribution width of the N sample data in the counting signal is substantially larger than a width of a single pulse in the counting signal, smaller than a baseline shift width, and larger than twice the sum of widths of all pulses in the distribution width; and
means for selecting a ½Nth sample data B of the N sample data in the sampling sequence;
means for subtracting the sample data A from the sample data B; and
means for outputting the result of subtraction of the sample data A from the sample data B as baseline removed data.

15. The system of claim 14, further comprising:
means for storing the sample data to be sorted in storage space with the values of the N sample data to be sorted as addresses of a storage unit and the numbers of the data of the same values as storage values in the storage unit with corresponding addresses;
means for accumulating the storage values of the data in the storage space from a lowest address to higher addresses to determine a current accumulating address N1 at which the accumulated value is equal to ½N −P, wherein P is an integer equal to or larger than zero (0) and smaller than ½N; and
means for outputting the current accumulating address N1 as the sample data A.

16. The system of claim 15, further comprising:
means for subtracting one (1) from the storage value in the storage unit with the same address as the value of a previous sample data of the N sample data, and adding one (1) to the storage value in the storage unit with the same address as the value of the newly input sample data.

17. A non-transitory computer-readable medium containing instructions stored therein for causing a computer processor to perform a method for processing a signal baseline, the method comprising:
sampling a counting signal to obtain sample data during a plurality of time periods;
sorting N sample data each time in a sampling sequence by magnitude;
outputting, among the N sample data, an arbitrary sample data A with a value equal to or smaller than a mid-value of the N sample data,
wherein a distribution width of the N sample data in the counting signal is substantially larger than a width of a single pulse in the counting signal, smaller than a baseline shift width, and larger than twice the sum of widths of all pulses in the distribution width; and
selecting a ½Nth sample data B of the N sample data in the sampling sequence,
subtracting the sample data A from the sample data B; and
outputting the result of the subtraction of the sample data A from the sample data B as baseline removed data.

18. The computer-readable medium of claim 17, wherein sorting the N sample data comprises:
storing the sample data to be sorted in storage space with the values of the N sample data to be sorted as addresses of a storage unit and the numbers of the data of the same values as storage values in the storage unit with corresponding addresses;
accumulating the storage values of the data in the storage space from a lowest address to higher addresses to determine a current accumulating address N1 at which the accumulated value is equal to ½N−P, wherein P is an integer equal to or larger than zero (0) and smaller than ½N; and
outputting the current accumulating address N1 as the sample data A.

19. The computer-readable medium of claim 18, the method further comprising, after inputting a new sample data:
subtracting one (1) from the storage value in the storage unit with the same address as the value of a previous sample data of the N sample data, and adding one (1) to the storage value in the storage unit with the same address as the value of the newly input sample data.

20. The computer-readable medium of claim 17, wherein the sample data A is the mid-value of the N sample data sorted by magnitude.

* * * * *